United States Patent [19]

Baklien et al.

[11] 4,106,924
[45] Aug. 15, 1978

[54] PESTICIDAL COMPOSITIONS

[75] Inventors: Asbjorn Baklien, Kingsbury; Alexandru Serban; Jocelyn Margaret Gregory, both of Croydon, all of Australia

[73] Assignee: ICI Australia Limited, Melbourne, Australia

[21] Appl. No.: 472,308

[22] Filed: May 22, 1974

Related U.S. Application Data

[62] Division of Ser. No. 551,520, May 20, 1966, abandoned.

[51] Int. Cl.$^2$ ............................................. A01N 9/24
[52] U.S. Cl. ........................................ 71/106; 560/136; 424/300
[58] Field of Search ............... 71/106, 122; 260/479 C

[56] References Cited

U.S. PATENT DOCUMENTS

| | | | |
|---|---|---|---|
| 2,344,063 | 3/1944 | Schotte et al. | 71/122 |
| 2,933,383 | 4/1960 | Lambrech | 71/106 |
| 3,165,392 | 1/1965 | Koopman | 71/122 |
| 3,255,227 | 6/1966 | Weil | 71/122 |
| 3,308,018 | 3/1967 | Gier et al. | 260/479 C |
| 3,391,180 | 7/1968 | Haubein | 71/106 |
| 3,399,048 | 8/1968 | Herrett et al. | 71/106 |

OTHER PUBLICATIONS

Blanksma et al., "Substitution of Mobile Halogen Atoms, etc.," (1946) CA 41, pp. 5484–5485 (1947).

*Primary Examiner*—Glennon H. Hollrah
*Attorney, Agent, or Firm*—Cushman, Darby & Cushman

[57] ABSTRACT

A process of controlling the growth of undesired plant life which comprises treating the undesired plants with an effective amount of a compound of the general formula:

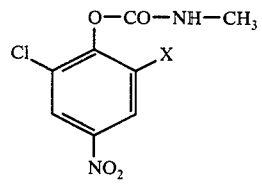

wherein X is chlorine, bromine or hydrogen and an inert carrier therefor.

1 Claim, No Drawings

PESTICIDAL COMPOSITIONS

This is a division, of application Ser. No. 551,520 filed May 20, 1966, now abandoned.

The present invention relates to new and useful pesticidal and herbicidal carbamic acid esters; in particular it relates to halogenated nitrophenyl carbamic acid esters and to processes for the production thereof.

Accordingly we provide new compounds of the general formula

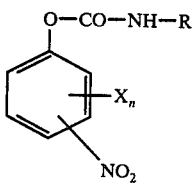

wherein X is a halogen selected from the group consisting of chlorine and bromine and, whenever there is more than one X the substituents X may be the same or different, n is an integer from 1 to 4 inclusive and R is hydrogen or an alkyl group containing from 1 to 10 carbon atoms.

Compounds according to our invention are e.g. 2-chloro-4-nitrophenyl N-methylcarbamate, 2,6-dichloro-4-nitrophenyl N-methylcarbamate, 2,6-dibromo-4-nitrophenyl N-methylcarbamate, 2,4,6-tribromo-3-nitrophenyl N-methylcarbamate, 2-bromo-6-chloro-4-nitrophenyl N-methylcarbamate, 2-chloro-6-nitrophenyl N-methylcarbamate, 3-chloro-4-nitrophenyl N-methylcarbamate, 2,6-dichloro-4-nitrophenyl N-ethylcarbamate, 2,6-dichloro-4-nitrophenyl N-propylcarbamate, 2,6-dichloro-4-nitrophenyl N-butylcarbamate, 2,6-dichloro-4-nitrophenyl carbamate, 2,6-dichloro-4-nitrophenyl N-decylcarbamate, 4-chloro-2-nitrophenyl N-methylcarbamate, 2-bromo-4-nitrophenyl N-methylcarbamate, 4-bromo-2-nitrophenyl N-methylcarbamate.

We have found that the compounds according to this invention show good pesticidal, in particular herbicidal properties. Many of our compounds also show biocidal activity against insects and fungi.

Accordingly we also provide a new composition of matter comprising firstly, as the active ingredient, at least one carbamic acid ester of the general formula

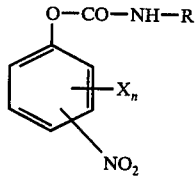

wherein X is a halogen selected from the group consisting of chlorine and bromine and, whenever there is more than one X, the substituents X may be the same or different, n is an integer from 1 to 4 inclusive and R is hydrogen or an alkyl group containing from 1 to 10 carbon atoms and secondly an inert carrier.

By inert carrier we mean either a liquid or a solid diluent used to obtain the desired concentration and to facilitate handling. For most purposes liquid formulations to be used in sprays are most convenient and among these again, aqueous liquid formulations are preferred. The latter may conveniently be prepared from emulsifiable solutions of the active compounds in organic solvents by dissolving the active ingredients in a solvent which is non-phytocidal to the plant medium from which the weed is to be removed, e.g. in xylene, toluene, kerosene or the methylated naphthalenes, adding an emulsifier and/or wetting agent and emulsifying the solution in water. A typical emulsifiable concentrate composition of this type would comprise 20% of 2,6-dichloro-4-nitrophenyl N-methylcarbamate, 40% kerosene, 35% xylene and 5% of an alkyl aryl polyether alchol emulsifier, all quantities on a weight basis.

Alternatively our mixtures may also be formulated into dusts by combining them with solid inert carriers such as powdered chalk, talcs, kieselguhr, bentonite and other colloidal clays.

They may also be formulated as dispersible powders by milling the active ingredient to a fine powder, optionally, together with an inert solid carrier as above disclosed and adding furthermore a dispersing agent. The preferred dispersible powders comprise the active ingredient, finely ground with a colloidal clay together with a dispersing agent.

Suitable emulsifying and dispersing agents are known from the prior art; anionic, cationic and nonionic agents may be used. A suitable non-ionic emulsifier is e.g. the condensation product of nonylphenol with ethylene oxide available commercially under the Trade Mark "Lissapol" N; suitable dispersing agents are e.g. the disodium salt of dinaphthylmethane disulphonate, sodium lauryl sulphonate and the condensation product of alkylphenol with ethylene oxide available commercially under the Trade Mark "Lubrol" E.

We also provide a process of manufacturing the compounds of our invention which comprises reacting a halogenated nitrophenol of the formula

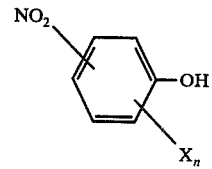

wherein X and n are as above defined, with an isocyanate R-NCO wherein R is as above defined, optionally in the presence of an inert solvent and, optionally and preferably, in the presence of a catalyst. Suitable catalysts are known, e.g. tertiary amines and dibutyl tin diacetate. Suitable inert solvents are e.g. petroleum ether, dioxan, tetrahydrofuran, ether, diisopropyl ether, hexane, isooctane and benzene.

The process may be represented by the equation:

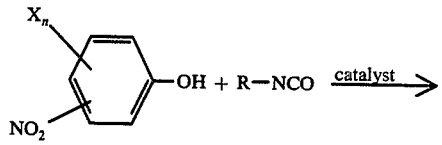
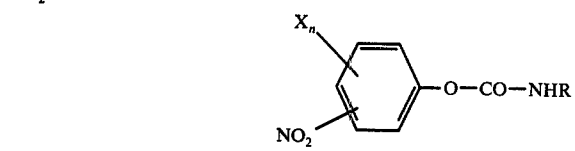

A further process according to our invention comprises reacting an alkali metal salt of the halogenated nitrophenol of the formula

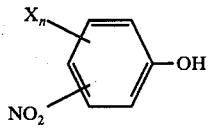

wherein X and n are as above defined, with phosgene in the presence of a solvent and reacting the resultant aryl chlorocarbonate with ammonia or an alkylamine in the presence of a base. Suitable solvents are e.g. benzene, toluene, chloroform and water. Suitable bases are e.g. aqueous solutions of hydroxides of the alkali metals, pyridine and tertiary amines. Suitable alkali metals are e.g. sodium and potassium.

The process may be represented by the equations

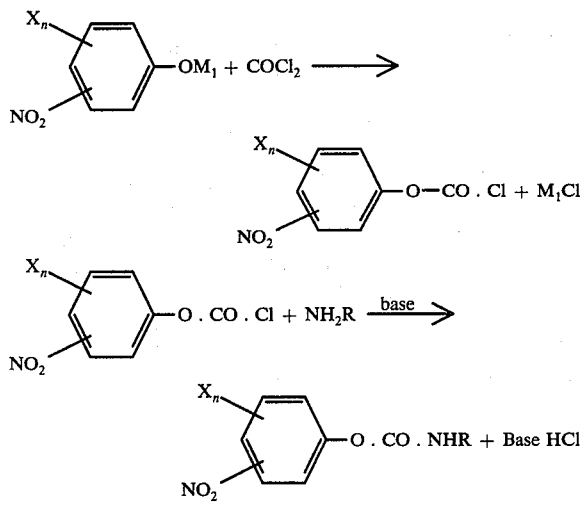

wherein $M_1$ is an alkali metal and R is as above defined.

Yet a further process according to our invention comprises reacting a halogenated nitrophenol of the formula

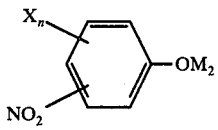

wherein X and n are as above defined and $M_2$ is an alkali metal or optionally hydrogen with a carbamoyl chloride R—NH.COCl, wherein R is as above defined, in the presence of a solvent and optionally in the presence of an acid acceptor. Suitable alkali metals are e.g. sodium and potassium. Suitable solvents are aromatic solvents e.g. benzene and toluene or chlorinated hydrocarbons e.g. chloroform. Suitable acid acceptors are tertiary amines, e.g. pyridine and the hydroxides and alkoxides of metals such as calcium, potassium and sodium.

The process may be represented by the equation

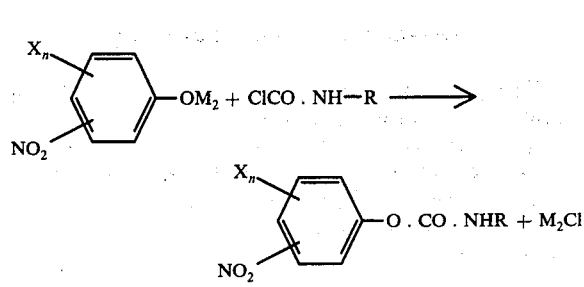

wherein X, n, $M_2$ and R are as above defined or by the equation

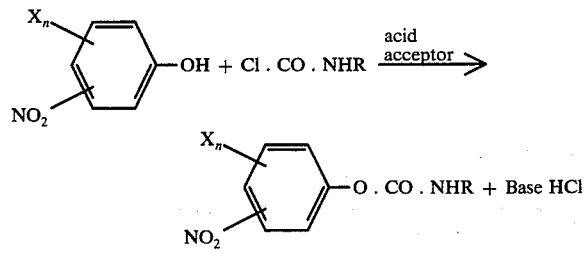

wherein X, n and R are as above defined.

The compounds of our invention have useful pesticidal, particularly herbicidal properties. Thus we have discovered that these compounds have a high herbicidal activity as a foliage post emergence spray at rates as low as ¼ lb per acre or less.

We also provide a process of controlling the growth of undesired plant life which comprises treating said undesired plants with a composition of this invention. Some of these compounds show high selectivity in that they are generally less active on narrow leaf plants than on broad leaf plants. In particular they show useful selectivity when applied to carrots and bean which are not damaged at application rates of 178 to 1 lb per acre. They are also highly effective against such plants as mustard seeds after a pre-emergence treatment has been applied.

When applied to plants at levels below the phytotoxic concentration certain compounds of our invention were also effective in controlling fungal growth for example of *Sclerotinia fructiola* (brown rot fungus). Accordingly we also provide a process of controlling fungal growth which comprises treating plants infested with fungus with compositions comprising compounds of our invention.

We have also found that compounds of our invention killed the mobile stages and eggs of *Tetranychus telarius* (red spider) especially on beans and carrots. Thus we also provide a process of eradicating undesired acarina which comprises treating media infested with acarina with compositions according to this invention.

The following examples illustrate the preparation of the compounds and compositions of our invention and their biological effects but are not to be construed as limiting.

EXAMPLE 1

2,6-Dichloro-4-nitrophenol (20.8 g) was added to a cooled solution of methyl isocyanate (6 ml) in dioxan (15 ml) in a pressure bottle. A few drops of triethylamine were added and the bottle was closed and shaken gently. An exothermic reaction took place and after standing for about 24 hours at room temperature, the mixture was diluted with 20 ml of petroleum ether and filtered to give 23.6 g of product having a melting point of 102°–103° C. A sample was re-crystallized from dioxan. The compound was identified by elemental analysis and by infra-red spectroscopy as being 2,6-dichloro-4-nitrophenyl N-methylcarbamate. It has a melting point of 104°–105° C. A 2% w/v aqueous dispersion of the compound was prepared by ball-milling 2 g of the compound in 100 ml of water containing 0.25 g of "Lubrol" E (Registered Trade Mark). This suspension was diluted as required with water and sprayed by hand through an "Aerograph" spray gun on to test plants at the rates indicated in Table I for assessment of post-emergence herbicidal activity. The test plants were growing in boxes 4½ inches × 4 inches × 3 inches; each box contained 1 row each of 3 or 4 species of plants which were one week old at the time of the spraying of the compound. Furthermore the compound was also tested for pre-emergence activity by spraying in the same manner as for the post emergence treatment on to soil in boxes 4½ inches × 4 inches × 3 inches in which seeds had been sown the day before spraying. Three weeks after applying the post emergence and pre-emergence spray treatments, the plants in the treated boxes were compared with those in untreated boxes, and assessed for response to the treatments using an arbitrary phytotoxicity scale of from 0 (no damage) to 5 (death).

Table I

Compound: 2,6-dichloro-4-nitrophenyl N-methylcarbamate
Phytotoxicity ratings at different application rates

| Application Rate | Post Emergence | | | Pre Emergence | | |
|---|---|---|---|---|---|---|
| (lb/acre) | ½ | 1 | 2 | 2 | 4 | 5 |
| Plant | | | | | | |
| Barnyard grass | 0 | 1 | 5 | 0 | 0 | — |
| Beans | 0 | 0 | 2 | — | — | — |
| Beet | — | 2 | 4 | — | — | — |
| Carrots | 0 | 0 | 2 | — | — | — |
| Clover | — | 0 | 1 | — | — | — |
| Cotton | — | 2 | 5 | 0 | 0 | — |
| Ipomea | — | 5 | — | — | — | 5 |
| Japanese millet | — | 2 | — | — | — | 0 |
| Lucerne | — | 0 | 0 | — | — | — |
| Maize | 0 | 0 | 0 | 0 | 0 | — |
| Mustard | 5 | 5 | 5 | — | 5 | 5 |
| Oats | — | 0 | — | — | 0 | 0 |
| Onion | 1 | 2 | 5 | — | — | — |
| Peas | 5 | 5 | 5 | — | — | 0 |
| Rice | 0 | 0 | 1 | 0 | 0 | — |
| Rye grass | 0 | 0 | 0 | — | — | 0 |
| Sorghum | 0 | 0 | 0 | 0 | 0 | — |
| Sunflower | — | 0 | — | — | — | 0 |
| Tomato | 5 | 5 | 5 | — | — | — |

— indicates that no tests were carried out.

The results shown in Table I show that 2,6-dichloro-4-nitrophenyl N-methylcarbamate has high herbicidal activity as a foliage (post emergence) spray at rates as low as ½ lb per acre and less. Moreover it shows high selectivity, being generally less active on narrow leaf plants e.g. maize, oats, rice and rye grass, than on broad leaf plants e.g. cotton, beet, ipomea, mustard, peas and tomato. Furthermore within the group of broad leaf plants it is also selective being less active on e.g. beans, clover, lucerne and sunflower than on cotton, beet, ipomea, mustard, peas and tomato. In particular it shows useful selectivity when applied to carrots and beans which it does not damage at rates of ½ to 1 lb per acre. The results in Table I also show that the compound is highly effective against mustard seeds after a pre-emergence treatment of 4 lb per acre has been applied.

EXAMPLE 2

A solution of 2-chloro-4-nitrophenol (17.4 g) and N,N-dimethyl aniline (12.5 g) in 100 ml of benzene was added dropwise and with stirring to a solution at 5° C of phosgene (15 g) in 50 ml of benzene. The mixture was stirred for 8 hours at room temperature; 50 g of ice was added to the reaction mixture and the phases separated. The benzene solution was washed with water, dried over anhydrous sodium sulphate and about one fifth of the solvent removed by distillation under reduced pressure. The remaining solution was added dropwise and with vigorous stirring at 5° C to 30 g of a 35% w/v aqueous solution of methylamine. Stirring was continued for 3 hours at room temperature. The benzene phase was separated, washed with water and dried over anhydrous sodium sulphate. Removal of the benzene by distillation under reduced pressure left 17 g of a crude product. This was re-crystallised from diisopropyl ether to yield straw yellow needles having a melting point of 113°–116° C and identified as 2-chloro-4-nitrophenyl N-methylcarbamate by elemental analysis and infra-red spectroscopy.

EXAMPLE 3

2-Nitro-4-chlorophenol (17.4 g) was dissolved in 25 ml of dioxan in a pressure bottle. 6.3 ml of methyl isocyanate were added followed by 2 drops of pyridine. The pressure bottle was closed and placed in a water bath maintained at a temperature of 60° C for 3 hours and then at room temperature for 24 hours. The reaction mixture was then diluted with 25 ml of petroleum ether and 18.8 g of crude product filtered off. The crude product was recrystallised from a mixture of ethanol and diisopropyl ether to yield pale yellow needles having a melting point of 131°–132° C with decomposition and identified as 4-chloro-2-nitrophenyl N-methylcarbamate by elemental analysis and infra-red spectroscopy.

EXAMPLE 4

2,6-Dibromo-4-nitrophenol (29.7 g) was dissolved in 30 ml of dioxan in a pressure bottle. An addition of 6.3 ml of methyl isocyanate followed by three drops of triethylamine was made. The pressure bottle was then closed and placed in a water bath maintained at 60° C for 2 hours and then at room temperature for 24 hours. 25 ml of petroleum ether were then added and 12.9 g of an impure crystalline product filtered off. The crude product was recrystallised from a mixture of ethanol and diisopropyl ether to yield long needles having a melting point of 147.5° to 148.5° C and identified as 2,6-dibromo-4-nitrophenol N-methylcarbamate by elemental analysis and infra-red spectroscopy.

EXAMPLE 5

The determination of herbicidal properties as described in Example 1 for 2,6-dichloro-4-nitrophenyl N-methylcarbamate was carried out with 2,6-dibromo-4-nitrophenyl N-methylcarbamate. The compound showed high herbicidal activity as a foliage spray at rates as low as ½ lb/acre, but it was less selective than the corresponding chloro compound. Results are shown in Table II.

Table II

Compound: 2,6-dibromo-4-nitrophenyl N-methylcarbamate
Phytotoxicity ratings at different application rates
as a post emergence foliage spray

| Plant | Application Rate (lb/acre) | | |
|---|---|---|---|
| | ½ | 1 | 2 |
| Barnyard grass | 0 | 0 | 0 |
| Beans | 0 | 3 | 3 |
| Beet | 0 | 0 | 0 |
| Carrots | 0 | 0 | 0 |
| Clover | 0 | 0 | 0 |
| Cotton | 0 | 0 | 3 |
| Lucerne | 0 | 0 | 1 |
| Maize | 0 | 0 | 0 |
| Mustard | 4 | 4 | 5 |
| Oats | 0 | 0 | 0 |
| Onion | 0 | 0 | 0 |
| Peas | 1 | 1 | 5 |
| Rice | 0 | 0 | 0 |
| Rye grass | 0 | 0 | 0 |
| Sorghum | 0 | 0 | 0 |
| Tomato | 0 | 0 | 0 |
| Wheat | 0 | 0 | 0 |

The scale is from 0 = no damage to 5 = death

EXAMPLE 6

The determination of herbicidal properties as described in Example 1 for 2,6-dichloro-4-nitrophenyl N-methylcarbamate was carried out with 2-chloro-4-nitrophenyl N-methylcarbamate.

This compound showed high herbicidal activity as a foliage spray at an application rate of 1 lb/acre. It also exhibited some pre-emergent activity when applied at the rate of 5 lb per acre.

Results are set out in Table III.

Table III

Compound: 2-Chloro-4-nitrophenyl N-methylcarbamate.
Phytotoxicity ratings at different application rates
as a post emergence (foliage) spray.

| Plant | Application Rate (lb/acre) | | |
|---|---|---|---|
| | 1 | 2 | 4 |
| Barnyard grass | 0 | 0 | 5 |
| Beans | 5 | 5 | 5 |
| Beet | 0 | 5 | 5 |
| Carrots | 0 | 3 | 4 |
| Clover | 0 | 0 | 0 |
| Cotton | 3 | 4 | 5 |
| Lucerne | 0 | 0 | 3 |
| Maize | 0 | 0 | 0 |
| Mustard | 5 | 5 | 5 |
| Oats | 0 | 0 | 3 |
| Onion | 5 | 5 | 5 |
| Peas | 3 | 3 | 4 |
| Rice | 0 | 0 | 4 |
| Rye grass | 0 | 0 | 4 |
| Sorghum | 0 | 0 | 5 |
| Tomato | 5 | 5 | 5 |
| Wheat | 0 | 0 | 3 |

As a pre-emergence spray when applied at the rate of 5 lb/acre its herbicidal effect was rated as 0 for both oats and wheat and 2 for mustard. The scale is from 0 = no damage to 5 = death.

As a pre-emergence spray when applied at the rate of 5 lb/acre its herbicidal effect was rated as 0 for both oats and wheat and 2 for mustard.

The scale is from 0 = no damage to 5 = death.

EXAMPLE 7

The determination of herbicidal properties as described in Example 1 for 2,6-dichloro-4-nitrophenyl N-methylcarbamate was carried out with 2-nitro-4-chlorophenyl N-methylcarbamate.

This compound showed considerable herbicidal activity as a foliage spray at an application rate of 20 lb/acre. It was effective on mustard at an application rate of 5 lb per acre.

The results are given in Table IV.

Table IV

Compound: 2-Nitro-4-chlorophenyl N-methylcarbamate
Phytotoxicity ratings at different application rates
as a post emergence (foliage) spray

| Plant | Application Rate (lb/acre) | | |
|---|---|---|---|
| | 1 | 5 | 20 |
| Millet | 0 | 0 | 0 |
| Mustard | 0 | 5 | 5 |
| Oats | 0 | 0 | 0 |
| Peas | 0 | 0 | 5 |
| Rye grass | 0 | 0 | 0 |
| Sunflower | 0 | 0 | 5 |

The scale is from 0 = no damage to 5 = death.

EXAMPLES 8 TO 14

Using the method for the preparation of 2,6-dichloro-4-nitrophenyl N-methylcarbamate described in Example 1, further compounds were prepared. The starting materials, the compound obtained, and the melting point of the compound obtained are set out in Table V.

Table V

| Ex. No. | Starting Materials | Product Obtained | Melting Point of Product °C |
|---|---|---|---|
| 8 | 2,4,6-tribromo-3-nitrophenol and methyl isocyanate | 2,4,6-tribromo-3-nitrophenyl N-methyl carbamate | 126–8 |
| 9 | 2-bromo-6-chloro-4-nitrophenol and methyl isocyanate | 2-bromo-6-chloro-4-nitrophenyl N-methyl carbamate | 137–9 |
| 10 | 2-chloro-6-nitrophenol and methyl isocyanate | 2-chloro-6-nitrophenyl N-methyl carbamate | 133–4 |
| 11 | 2,6-dichloro-4-nitrophenol and ethyl isocyanate | 2,6-dichloro-4-nitrophenyl N-ethyl carbamate | 128–130 |
| 12 | 2,6-dichloro-4-nitrophenol and n-propyl isocyanate | 2,6-dichloro-4-nitrophenyl N-(n-propyl)carbamate | 125–7 |
| 13 | 2,6-dichloro-4-nitrophenol and n-butyl isocyanate | 2,6-dichloro-4-nitrophenyl N-(n-butyl) carbamate | 115–7 |
| 14 | 2,6-dichloro-4-nitrophenol and n-decyl isocyanate | 2,6-dichloro-4-nitrophenyl N-(n-decyl)carbamate | 92–3 |

EXAMPLES 15 TO 20

The determination of herbicidal properties as described in Example 1 for 2,6-dichloro-4-nitrophenyl N-methyl carbamate was carried out singly with each of the compounds prepared in Examples 8 to 13 inclusive.

Each of these compounds showed high herbicidal activity as a foliage spray at an application rate of 2 lb per acre and in the case of some plants they were effective as herbicides at rates of application as low as 0.5 lb per acre. The results are given in Table VI.

Table VI

| Ex. No. | 15 | | | 16 | | | 17 | | | 18 | | | 19 | | | 20 | | |
|---|---|---|---|---|---|---|---|---|---|---|---|---|---|---|---|---|---|---|
| Compound | 2,4,6-tribrom-3-nitrophenyl N-methyl carbamate | | | 2-bromo-6-chloro-4-nitrophenyl N-methyl carbamate | | | 2-chloro-6-nitrophenyl N-methyl carbamate | | | 2,6-dichloro-4-nitrophenyl N-ethyl carbamate | | | 2,6-dichloro-4-nitrophenyl N-(n-propyl)-carbamate | | | 2,6-dichloro-4-nitrophenyl N-(n-butyl)-carbamate | | |
| Application Rate (lb/acre) | ½ | 1 | 2 | ½ | 1 | 2 | ½ | 1 | 2 | ½ | 1 | 2 | ½ | 1 | 2 | ½ | 1 | 2 |
| Mustard | 5 | 5 | 5 | 0 | 0 | 4 | 0 | 0 | 0 | 5 | 5 | 5 | 5 | 5 | 5 | 3 | 5 | 5 |
| Carrot | 2 | 3 | 5 | — | — | — | 0 | 0 | 3 | 0 | 0 | 3 | 0 | 1 | 3 | 0 | 0 | 0 |
| Japanese millet | — | — | — | 0 | 0 | 3 | 0 | 0 | 3 | 0 | 2 | 5 | 0 | 1 | 5 | 0 | 2 | 5 |
| Ipomea | — | — | — | 0 | 2 | 5 | 0 | 2 | 5 | 5 | 5 | 5 | 4 | 5 | 5 | 4 | 5 | 5 |
| Sunflower | — | — | — | 0 | 0 | 4 | 0 | 0 | 2 | 5 | 5 | 5 | 5 | 5 | 5 | 5 | 5 | 5 |
| Lucerne | 1 | 3 | 5 | — | — | — | 5 | 5 | 5 | — | — | — | — | — | — | — | — | — |
| Barnyard grass | 1 | 2 | 5 | — | — | — | — | — | — | — | — | — | — | — | — | — | — | — |

The scale is from 0 = no damage to 5 = death.
— indicates that no tests were carried out.

EXAMPLE 21

The determination of herbicidal properties as described in Example 1 was carried out except that instead of using different species of test plants, use was made of only one species of test plant namely *Emex australis* commonly known as spiny emex or double gee. The 2,6-dichloro-4-nitrophenyl N-methyl carbamate showed high herbicidal activity as a foliage spray at application rates of 4, 2 and 1 lb per acre. At these application rates it did not damage pasture plants e.g. clover and lucerne neither did it affect cereal crops e.g. rye, wheat and oats.

EXAMPLE 22

Seed dressings were prepared from 2-nitro-4-chlorophenyl N-methyl carbamate made as described in Example 3 by ball milling the compounds with china clay to give concentrations of the active compound of 6.25% w/w, 12.5% w/w and 25% w/w. Seed of the wheat variety Olympic was inoculated by thorough mixing with 0.5% of its weight of spores of either of two strains of the bunt fungus *Tilletia caries* one strain being susceptible, the other strain being resistant or tolerant to the commercial seed dressing hexachlorobenzene. Portions of both the inocculated wheat seeds were dressed with 125, 250 and 500 parts per million parts of inocculated wheat of either 2-nitro-4-chlorophenyl-N-methyl carbamate or hexachlorobenzene by mixing them thoroughly in a jar roller mill. The inocculated wheat seed treated as described above and seed which had been inocculated but not treated with the active compounds were then sown in 6" diameter earthenware pots at the rate of 15 seeds per pot in moistened sandy loam taken from wheat growing land. The pots and their contents were held at about 8° C for 16 days to encourage spore germination and development. They were then transferred to a glass house held at about 25° C and after 8 weeks the wheat plants had formed ears which were assessed for presence or absence of bunted grain.

Results are shown in Table VII.

Table VII

| Bunt strain | Dressing rate of compound ppm | Percentage of bunt | |
|---|---|---|---|
| | | Hexa-chloro-benzene | 2-nitro-4 chloro-phenyl N-methyl carbamate |
| Susceptible to hexachlorobenzene | 0 | 43.5 | 43.5 |
| | 125 | 11.8 | 3.2 |
| | 250 | 0.2 | 0.0 |
| | 500 | 0.0 | 0.0 |
| Resistant to hexachlorobenzene | 0 | 47.4 | 47.4 |
| | 125 | 50.0 | 4.3 |
| | 250 | 31.2 | 0.0 |
| | 500 | 19.3 | 0.0 |

We claim:

1. The process of controlling the growth of undesired plant life which comprises treating said undesired plants with an effective amount of 2-chloro-4-nitrophenyl N-methyl carbamate.

* * * * *